(12) United States Patent
Chen et al.

(10) Patent No.: US 9,724,000 B2
(45) Date of Patent: Aug. 8, 2017

(54) EXERCISE GUIDING SYSTEM, EXERCISE GUIDING METHOD AND ANAEROBIC THRESHOLD MEASURING METHOD

(71) Applicant: Industrial Technology Research Institute, Hsinchu (TW)

(72) Inventors: Rong-Rong Chen, Taipei (TW); Yueh-Hsuan Lee, Hsinchu (TW); Tung-Hung Lu, Yilan County (TW); Jong-Shyan Wang, Taoyuan County (TW); Hsing-Hua Tsai, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 277 days.

(21) Appl. No.: 14/574,392

(22) Filed: Dec. 18, 2014

(65) Prior Publication Data
US 2015/0273313 A1 Oct. 1, 2015

Related U.S. Application Data

(60) Provisional application No. 61/970,907, filed on Mar. 27, 2014.

(30) Foreign Application Priority Data

Oct. 20, 2014 (TW) .............................. 103136140 A

(51) Int. Cl.
*A63F 13/00* (2014.01)
*A61B 5/024* (2006.01)
(Continued)

(52) U.S. Cl.
CPC .......... *A61B 5/024* (2013.01); *A61B 5/02405* (2013.01); *A61B 5/1118* (2013.01); *A61B 5/4866* (2013.01); *A61B 5/0456* (2013.01)

(58) Field of Classification Search
CPC ... A63F 13/212; A63B 24/00; A63B 2230/04; A63B 2230/06
See application file for complete search history.

(56) References Cited

U.S. PATENT DOCUMENTS 4,578,769 A 3/1986 Frederick
6,301,499 B1 * 10/2001 Carlson .................. A61B 5/222
600/510

(Continued)

FOREIGN PATENT DOCUMENTS

| CN | 1389176 | 1/2003 |
|---|---|---|
| CN | 101636107 | 1/2010 |
| TW | I393550 | 4/2013 |

OTHER PUBLICATIONS

"Office Action of Taiwan Counterpart Application", issued on Aug. 4, 2015, p. 1-p. 6.

(Continued)

*Primary Examiner* — James S McClellan
(74) *Attorney, Agent, or Firm* — Jianq Chyun IP Office

(57) ABSTRACT

The present disclosure provides an exercise guiding system including a sensing module, a calculating module, a converting module and an output module. The sensing module keeps recording an R-R interval of a user doing exercise. The computing module receives the R-R interval from the sensing module and performs heart rate variability analysis on the R-R interval to generate a first output. The converting module receives the first output from the calculating module, recognizes a threshold output of the first output according to a threshold and acquires an anaerobic threshold corresponding to the user according to the threshold output, wherein the anaerobic threshold corresponding to the user is a first heart rate corresponding to the threshold output in the R-R interval. The output module receives the anaerobic threshold from the converting module and outputs an exer- (Continued)

cise guidance of the user according to the anaerobic threshold.

23 Claims, 8 Drawing Sheets

(51) Int. Cl.
*A61B 5/11* (2006.01)
*A61B 5/00* (2006.01)
A61B 5/0456 (2006.01)

(56) References Cited

U.S. PATENT DOCUMENTS

| | | | |
|---|---|---|---|
| 6,512,948 B1 | 1/2003 | Shiga et al. | |
| 6,920,348 B2 | 7/2005 | Vasin et al. | |
| 8,241,184 B2 | 8/2012 | DiBenedetto et al. | |
| 8,360,936 B2 | 1/2013 | DiBenedetto et al. | |
| 8,485,661 B2 | 7/2013 | Yoo et al. | |
| 8,499,476 B2 | 8/2013 | Berner, Jr. et al. | |
| 8,516,723 B2 | 8/2013 | Ferrigan et al. | |
| 8,600,699 B2 | 12/2013 | Vock et al. | |
| 2006/0063980 A1 | 3/2006 | Hwang et al. | |
| 2006/0079800 A1* | 4/2006 | Martikka | A61B 5/0488 600/546 |
| 2007/0006489 A1 | 1/2007 | Case et al. | |
| 2009/0149299 A1 | 6/2009 | Tchao et al. | |
| 2010/0191127 A1* | 7/2010 | Keren | A61B 5/02028 600/484 |
| 2011/0027766 A1 | 2/2011 | Yoo et al. | |
| 2011/0130643 A1 | 6/2011 | Derchak et al. | |
| 2012/0015779 A1 | 1/2012 | Powch et al. | |
| 2012/0047132 A1 | 2/2012 | Fleming et al. | |
| 2012/0173978 A1 | 7/2012 | Lee et al. | |
| 2012/0244995 A1 | 9/2012 | DiBenedetto et al. | |
| 2012/0253484 A1 | 10/2012 | Burich et al. | |
| 2012/0254934 A1 | 10/2012 | McBrearty et al. | |
| 2012/0258433 A1 | 10/2012 | Hope et al. | |
| 2012/0265326 A1 | 10/2012 | Prstojevich et al. | |
| 2013/0276201 A1 | 10/2013 | Pezzimenti | |
| 2014/0073486 A1* | 3/2014 | Ahmed | A61B 5/02405 482/9 |
| 2014/0074407 A1* | 3/2014 | Hernandez-Silveira | A61B 5/1118 702/19 |
| 2014/0141937 A1 | 5/2014 | Kim et al. | |

OTHER PUBLICATIONS

Karavirta et al., "Heart Rate Dynamics after Combined Endurance and Strength Training in Older Men," Medicine and Science in Sports and Exercise, Jul. 2009, pp. 1436-1443.

Willson et al., "Relationship between detrended fluctuation analysis and spectral analysis of heart-rate variability," Physiological Measurement, May 2002, pp. 385-401.

Ho et al., "Predicting survival in heart failure case and control subjects by use of fully automated methods for deriving nonlinear and conventional indices of heart rate dynamics," Circulation, Aug. 5, 1997, pp. 842-848.

Huikuri et al., "Fractal Correlation Properties of R-R Interval Dynamics and Mortality in Patients With Depressed Left Ventricular Function After an Acute Myocardial Infarction," Circulation, Jan. 4-11, 2000, pp. 47-53.

Yeh et al., "Detrended fluctuation analyses of short-term heart rate variability in surgical intensive care units," Biomedical Engineering: Applications, Basis and Communications, Apr. 2006, pp. 67-72.

* cited by examiner

| Watt | Time (minute) | First output α1 | Heart rate |
|---|---|---|---|
| 0 | 6 | 1.472 | 95 |
| 0 | 7 | 1.605 | 101 |
| 30 | 8 | 1.507 | 108 |
| 30 | 9 | 1.128 | 105 |
| 30 | 10 | 1.265 | 105 |
| 60 | 11 | 1.432 | 116 |
| 60 | 12 | 1.341 | 120 |
| 60 | 13 | 1.175 | 119 |
| 90 | 14 | 1.163 | 126 |
| 90 | 15 | 1.134 | 126 |
| 90 | 16 | 0.933 | 136 |
| 120 | 17 | 0.856 | 145 |
| 120 | 18 | 0.99 | 149 |
| 120 | 19 | 0.932 | 153 |
| 140 | 20 | 0.874 | 159 |
| 140 | 21 | 0.76 | 157 |
| 140 | 22 | 0.913 | 167 |

FIG. 3

| Watt | Time (minute) | Sample 1 | | | Sample 2 | | | Sample 3 | | |
|---|---|---|---|---|---|---|---|---|---|---|
| | | $\alpha 1$ | RER | HR | $\alpha 1$ | RER | HR | $\alpha 1$ | RER | HR |
| 0 | 6 | 1.472 | 0.82 | 95 | 1.462 | 0.86 | 103 | 0.776 | 0.93 | 67 |
| 0 | 7 | 1.605 | 0.78 | 101 | 1.425 | 0.78 | 105 | 0.776 | 0.86 | 72 |
| 30 | 8 | 1.507 | 0.78 | 108 | 1.379 | 0.74 | 103 | 0.886 | 0.84 | 71 |
| 30 | 9 | 1.128 | 0.78 | 105 | 1.3 | 0.77 | 108 | 1 | 0.84 | 77 |
| 30 | 10 | 1.265 | 0.78 | 105 | 1.406 | 0.77 | 107 | 1.043 | 0.78 | 77 |
| 60 | 11 | 1.432 | 0.87 | 116 | 1.248 | 0.72 | 102 | 1.15 | 0.83 | 74 |
| 60 | 12 | 1.341 | 0.87 | 120 | 1.349 | 0.71 | 113 | 1.146 | 0.79 | 81 |
| 60 | 13 | 1.175 | 0.86 | 119 | 1.36 | 0.77 | 115 | 1.132 | 0.81 | 90 |
| 90 | 14 | 1.163 | 0.83 | 126 | 1.462 | 0.8 | 121 | 1.065 | 0.9 | 88 |
| 90 | 15 | 1.134 | 0.91 | 126 | 1.184 | 0.88 | 126 | 1.177 | 0.89 | 95 |
| 90 | 16 | 0.933 | 0.95 | 136 | 1.125 | 0.88 | 127 | 1.139 | 0.94 | 96 |
| 120 | 17 | 0.856 | 0.99 | 145 | 1.297 | 0.9 | 129 | 0.936 | 0.92 | 100 |
| 120 | 18 | 0.931 | 0.99 | 149 | 1.083 | 0.92 | 144 | 1.085 | 0.96 | 107 |
| 120 | 19 | 0.932 | 1 | 153 | 1.206 | 0.96 | 145 | 1.017 | 0.99 | 108 |
| 140 | 20 | 0.874 | 1 | 159 | 1.06 | 0.98 | 148 | 0.862 | 0.98 | 115 |
| 140 | 21 | 0.76 | 1.01 | 157 | 1.026 | 1 | 163 | 1.009 | 1 | 119 |
| 140 | 22 | 0.913 | 1 | 167 | 0.964 | 1.02 | 162 | 0.896 | 1.01 | 120 |
| 160 | 23 | 0.865 | 1.01 | 171 | 0.89 | 1.01 | 167 | 0.932 | 1.01 | 122 |
| 160 | 24 | 0.766 | 1 | 171 | 0.781 | 1.01 | 169 | 0.947 | 1.01 | 125 |
| 160 | 25 | 0.81 | 1.09 | 176 | 0.808 | 1.03 | 174 | 0.963 | 1.01 | 129 |
| 180 | 26 | 0.68 | 1.1 | 185 | 0.57 | 1.07 | 178 | 0.719 | 1.01 | 135 |
| 180 | 27 | 0.763 | 1.1 | 187 | 0.559 | 1.09 | 182 | 0.668 | 1.01 | 139 |
| 180 | 28 | 0.792 | 1.1 | 191 | 0.56 | 1.09 | 184 | 0.852 | 1.06 | 143 |
| 200 | 29 | 0.857 | 1.11 | 198 | 0.686 | 1.13 | 187 | 0.708 | 1.09 | 156 |
| 200 | 30 | 0.584 | 1.14 | 204 | 0.56 | 1.14 | 190 | 0.663 | 1.09 | 156 |
| 200 | 31 | 0.482 | 1.16 | 208 | 0.755 | 1.18 | 194 | 0.553 | 1.08 | 159 |

FIG. 7

| Sample | General equation | Present disclosure | Gas analyzer |
|---|---|---|---|
| Sample 1 | (220-27)*80%=154 | 145 | 153 |
| Sample 2 | (220-27)*80%=154 | 167 | 163 |
| Sample 3 | (220-27)*80%=154 | 122 | 119 |

FIG. 8

| Sample | General equation | Present disclosure | Gas analyzer | Error |
|---|---|---|---|---|
| Sample 1 | 80% | 145/(220-27)=75% | 153/(220-27)=79% | 4% |
| Sample 2 | 80% | 167/(220-27)=86% | 163/(220-27)=87% | 1% |
| Sample 3 | 80% | 122/(220-27)=63% | 119/(220-27)=62% | 1% |

FIG. 9

| Respiratory exchange rate (RER) of gas analyzer | First output value α1 of the disclosure | Energy consumption | Exercise state |
|---|---|---|---|
| <0.85 | <threshold output and in an exercise state | Fat | Low strength exercise |
| 0.85–1.00 | <threshold output and in a non-exercise state | Protein | Rest state |
| >1.00 | >threshold output | Glucose | High strength exercise |

FIG. 11

EXERCISE GUIDING SYSTEM, EXERCISE GUIDING METHOD AND ANAEROBIC THRESHOLD MEASURING METHOD

CROSS-REFERENCE TO RELATED APPLICATION

This application claims the priority benefits of U.S. provisional application Ser. No. 61/970,907, filed on Mar. 27, 2014 and Taiwan application serial no. 103136140, filed on Oct. 20, 2014. The entirety of each of the above-mentioned patent applications is hereby incorporated by reference herein and made a part of this specification.

BACKGROUND

Technical Field

The disclosure relates to an exercise guiding system, an exercise guiding method and an anaerobic threshold measuring method, and particularly relates to an exercise guiding system, an exercise guiding method and an anaerobic threshold measuring method capable of using an R-R interval of a user to calculate an anaerobic threshold.

Related Art

In view of various bodybuilding methods and projects, based on energy metabolism methods and energy supplying methods thereof, three basic exercise forms including aerobic exercise, anaerobic exercise and mixed exercise including the aerobic exercise and anaerobic exercise are concluded. Generally, the aerobic exercise is a an exercise form with a long exercise time and a middle-low exercise intensity, which may produce carbon dioxide and water through fat metabolism, such that fat in the body is consumed during the exercise process to achieve a weight losing effect. The anaerobic exercise is an exercise form with a short exercise time and high exercise intensity, and through adenosine triphosphate (ATP) metabolism, creatine phosphate metabolism and carbohydrate metabolism, a large amount of muscle glycogen and liver glycogen is consumed during the exercise process, so that the weight losing effect is lower. Moreover, a metabolite of the anaerobic exercise is lactic acid or lactate, and if the human body is kept in the anaerobic exercise state, the lactic acid or lactate is quickly accumulated, which may cause muscle fatigue to stop the exercise.

A commonly used determination index of the anaerobic exercise includes a maximal oxygen uptake ($VO_2$ max) and an anaerobic threshold (AT).

The $VO_2$ max is the maximum amount of oxygen utilized or consumed by histiocytes when a person is engaged in the most intense sport on a sea level. The $VO_2$ max can be used to evaluate an aerobic work energy and cardiopulmonary endurance of a person, and can be used to set a training intensity of endurance exercise of an athlete. Generally, a unit of the $VO_2$ max can be represented by an absolute oxygen uptake L/min, or represented by a relative unit weight uptake ml/kg/min. The $VO_2$ max of a general male adult is about 30-40 ml/kg/min, and the $VO_2$ max of a professional athlete such as a bicyclist or a distance runner can be 80 ml/kg/min. Since an estimation method of the $VO_2$ max requires the user to engage in an intense exercise, it is not suitable for children and elders. Moreover, sine an inspection instrument of the $VO_2$ max has a high price, it is not easy to promote the inspection instrument to the mass market.

The anaerobic threshold is a turning point when an energy system of the human body is changed from the aerobic exercise to the anaerobic exercise, i.e. a turning point of metabolism when the human body starts to accumulate lactic acid. The anaerobic threshold is varied along with different physical fitness conditions of human body. Determination of the anaerobic threshold includes direct measurement of blood lactate, respiratory exchange ratio and heart rate, etc. In an actual measurement, measurement of blood lactate and respiration rate is not convenient (which requires blood drawing and expensive instrument), and measurement of the heart rate is the simplest and most convenient.

Related technique discloses a method for measuring the anaerobic threshold by using heartbeat specific information. According to the above method, predetermined personal information including age, weight, sex, etc. is used to obtain the highest heart rate to serve as a determination basis for the anaerobic threshold. However, the heart rate corresponding to the anaerobic respiration is not necessarily the highest heart rate. In other words, when two users with the same age and different physical fitness conditions adopt the above method to deduce the anaerobic thresholds, the measured anaerobic thresholds may have an error.

Therefore, it is important to ameliorate the anaerobic threshold measuring method and provide an effective and convenient exercise guiding system capable of analysing the anaerobic threshold to provide an exercise guidance according to an individual physical fitness condition.

SUMMARY

The disclosure is directed to an exercise guiding system, an exercise guiding method and an anaerobic threshold measuring method, by which an R-R interval of a user is measured to generate an anaerobic threshold corresponding to the user without using an expensive instrument, so as to provide the user a suitable exercise guidance.

An exemplary embodiment of the disclosure provides an exercise guiding system including a sensing module, a calculating module, a converting module and an output module. The sensing module keeps recording an R-R interval of a user doing exercise. The calculating module is coupled to the sensing module, and receives the R-R interval corresponding to the user from the sensing module and performs a heart rate variability analysis on the R-R interval to generate a first output. The converting module is coupled to the calculating module, and receives the first output from the calculating module, recognizes a threshold output of the first output according to a threshold and acquires an anaerobic threshold corresponding to the user according to the threshold output, wherein the anaerobic threshold corresponding to the user is a first heart rate corresponding to the threshold output in the R-R interval. The output module is coupled to the converting module, and receives the anaerobic threshold from the converting module and outputs an exercise guidance of the user according to the anaerobic threshold.

An exemplary embodiment of the disclosure provides an exercise guiding method which includes following steps. An R-R interval of a user doing exercise is kept recording. A heart rate variability analysis is performed on the R-R interval to generate a first output. A threshold output of the first output is recognized according to a threshold, and an anaerobic threshold corresponding to the user is acquired according to the threshold output, wherein the anaerobic threshold corresponding to the user is a first heart rate corresponding to the threshold output in the R-R interval. An exercise guidance of the user is output according to the anaerobic threshold.

An exemplary embodiment of the disclosure provides an anaerobic threshold measuring method, which includes following steps. A time sequence of an R-R interval corresponding to a user is calculated. The time sequence is calculated to generate an R-R interval self-similarity parameter. A threshold parameter in the R-R interval self-similarity parameter is recognized according to a threshold, and an anaerobic threshold corresponding to the user is acquired according to the threshold parameter, wherein the anaerobic threshold corresponding to the user is a first heart rate corresponding to the threshold parameter in the R-R interval.

According to the above descriptions, in the exercise guiding system, the exercise guiding method and the anaerobic threshold measuring method of the invention, the R-R interval of the user doing exercise is measured, and the R-R interval self-similarity parameter is calculated according to the R-R interval, and the anaerobic threshold corresponding to the user is acquired, so as to provide the user a suitable exercise guidance.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

FIG. 3 is a table listing first outputs calculated by the exercise guiding system of the disclosure and corresponding heart rates.

FIG. 7 is a comparison table of anaerobic thresholds obtained by using a gas analyser through a $VO_2$ max test and obtained through calculation of the exercise guiding system of the disclosure.

FIG. 8 is a comparison table of anaerobic thresholds obtained by using a general equation, the exercise guiding system of the disclosure and a gas analyser through the $VO_2$ max test.

FIG. 9 is a comparison table of percentages between heart rates corresponding to an anaerobic exercise and the maximum heart rate that are inversely deduced according to anaerobic thresholds obtained by using the general equation, the exercise guiding system of the disclosure and the gas analyser through the $VO_2$ max test.

FIG. 11 is a comparison table of energy supply mode analysis between the exercise guiding system of the disclosure and the $VO_2$ max test performed through the gas analyser.

DETAILED DESCRIPTION OF DISCLOSED EMBODIMENTS

Figure 1:
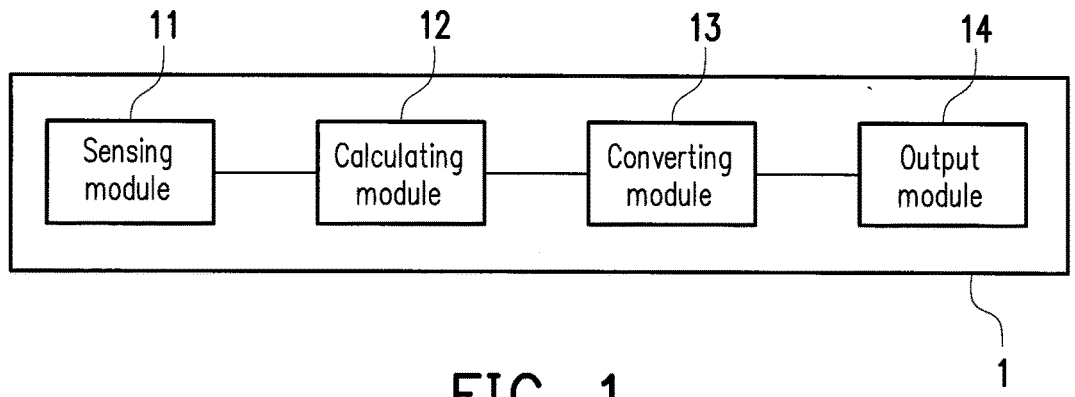
FIG. 1 is a block diagram of an exercise guiding system according to a first exemplary embodiment of the disclosure.

Terms used in the disclosure are defined as follows.

Anaerobic threshold: which refers to a turning point of metabolism when human body is changed from an aerobic energy system to an anaerobic energy system during exercise, and the anaerobic threshold can be digitised by a blood lactate, a respiratory exchange ratio and a heart rate, etc. In the disclosure, the anaerobic threshold is represented by the heart rate of the user when the user doing exercise enters an anaerobic respiration.

Maximal heart rate: which refers to a maximum value of a heartbeat frequency reached when an exercise strength of the user doing exercise increases, and is an index used for measuring whether the exercise strength is proper. In a general calculation formula, (220-age) is used for representing the maximal heart rate. Generally, when the exercise strength makes the heart rate of a sporter reaching 80% of the maximal heart rate, the sporter starts to enter the anaerobic exercise, i.e. a general calculation formula of the anaerobic threshold is (220-age)*80%.

R-R interval: which refers to an interval between heartbeats, and is generally represented by R-R interval of continuous heartbeats. In an electrocardiogram, R wave is an obvious waveform, and is easy to be detected, R interval represents a beating rate of heart, so that the R-R interval is generally used to represent the heartbeat interval. Namely, the R-R interval is a time interval of adjacent R waves on the electrocardiogram.

Heart rate variability (HRV) analysis: the HRV analysis is also referred to as heart rate variation degree analysis, which is a method for measuring a variation degree of continuous heart rates, and is an important method for estimating an automatic nervous system (ANS) function. A calculation method thereof is to analyse a time sequence of heartbeat intervals obtained through the electrocardiogram or pulse measurement. Besides the heartbeats caused by rhythmic discharge of the heart itself, the heart is also controlled by an ANS. A lot of literature in the past research has shown that there is a significant relationship between control of the ANS and a death rate related to cardiovascular diseases such as sudden cardiac death, hypertension, hemorrhagic shock, septic shock, etc. Clinically, the HRV analysis can also be used as an index to forecast a death rate after heart attack is occurred or can be used to forecast prognosis of late liver cancer patients, or applied to a plurality of pediatric diseases including congenital heart disease, myocarditis, diabetes, respiratory distress syndrome of newborn, sudden infant death syndrome, etc. Analysis patterns may include time domain analysis and frequency domain analysis, and in the disclosure, the time domain analysis and the frequency domain analysis of the HRV analysis are adopted.

Maximal oxygen uptake ($VO_2$ max): which is the maximum amount of oxygen utilized or consumed by histiocytes when a person is engaged in the most intense exercise. The $VO_2$ max can be used to evaluate an aerobic work energy and cardiopulmonary endurance of a person, and can be used to set an exercise training intensity of an athlete.

$VO_2$ max test: to use a stationary exercise bike to conduct exercise in a method of gradually increasing an exercise load, and during the exercise process, a gas analyser is used to collect and analyse an oxygen uptake, and the heart rate is taken as the exercise strength for entering the anaerobic threshold. A determination principle thereof is that when the respiratory exchange ratio (RER) is greater than 1, it represents that the user enters the anaerobic threshold.

First Exemplary Embodiment

FIG. 1 is a block diagram of an exercise guiding system according to the first exemplary embodiment of the disclosure.

Referring to FIG. 1, the exercise guiding system 1 can calculate an anaerobic threshold corresponding to a time point when the user doing exercise enters an anaerobic respiration according to an exercise status of the user doing exercise, and provide an exercise guidance according to the anaerobic threshold. It should be noticed that the exercise guiding system 1 can be installed on an electronic product, a portable electronic product, a watch, a wearable device, exercise equipment, a bicycle, a treadmill, glasses and a biosensor, etc., and exercises suitable for the exercise guiding system 1 includes at least one of a bicycle exercise, an aerobic exercise and running.

The exercise guiding system 1 includes a sensing module 11, a calculating module 12, a converting module 13 and an output module 14.

The sensing module 11 keeps recording a plurality sets of heartbeat information of a user doing exercise. Collection of the heartbeat information can be implemented through any in vitro sensor capable of detecting heartbeats of human body.

The in vitro sensor can be coupled to the sensing module 11, such that the sensing module 11 can record the heartbeat information of the user. For example, the heartbeat information of the disclosure is R-R interval. It should be noticed that although the sensing module 11 of the disclosure directly obtains the sensed R-R intervals of heartbeats of the user from the in vitro sensor, the disclosure is not limited thereto. For example, in another exemplary embodiment, the sensing module 11 can also calculate the R-R intervals of the heartbeats of the user according to user's heart rate detected by the in vitro sensor.

The calculating module 12 is coupled to the sensing module 11. The calculating module 12 receives the R-R intervals corresponding to the user from the sensing module 11 and performs a HRV analysis on the R-R intervals to generate a first output α1.

Figure 2:
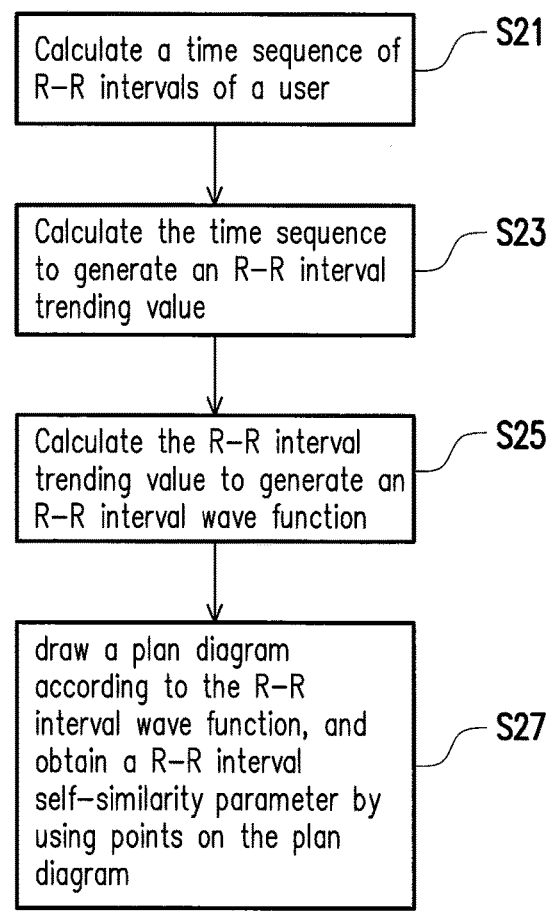
FIG. 2 is a flowchart illustrating a method for calculating a first output according to the first exemplary embodiment of the disclosure.

FIG. 2 is a flowchart illustrating a method for calculating the first output according to the first exemplary embodiment of the disclosure.

Referring to FIG. 2, in step S21, the calculating module 12 calculates a time sequence of R-R intervals of the user. For example, in the step S21, the calculating module 12 calculates a cumulative deviation between each heartbeat S(i) in the R-R intervals S of the user and an average heartbeat $\bar{S}$, so as to generate the time sequence $C(k)=\Sigma_{i=1}^{k} [S(i)-\bar{S}]$.

Then, in step S23, the calculating module 12 calculates the time sequence to generate an R-R interval trending value. For example, in the step S23, the calculating module 12 cuts the time sequence C(k) into a plurality of sections with a predetermined length n, and calculates a partial trending value $C_n(k)$ of each section according to a least square method, so as to generate the R-R interval trending value.

Then, in step S25, the calculating module 12 calculates the R-R interval trending value to generate an R-R interval wave function. For example, the calculating module 12 subtracts the time sequence C(k) by the partial trending value $C_n(k)$ of each section, and calculates a root mean square (RMS) of each section to generate the R-R interval wave function F(n):

$$F(n) = \sqrt{1/N \sum_{k=1}^{N} [C(k) - Cn(k)]^2}$$

Where, N represents a total length of the time sequence.

Finally, in step S27, the calculating module 12 draws a plan diagram according to the R-R interval wave function, and obtains an R-R interval self-similarity parameter by using points in the plan diagram, where the R-R interval self-similarity parameter is the aforementioned first output α1. For example, the calculating module 12 draws a plan diagram of logarithm, $\log_{10}F(n)$ relative to $\log_{10}(n)$, and calculates a linear equation of the points in the plan diagram according to the least square method, and calculates a slope of the linear equation to obtain the R-R interval self-similarity parameter (i.e. the first output α1).

Referring to FIG. 1, the converting module 13 is coupled to the calculating module 12. The converting module 13 receives the first output α1 from the calculating module 12, recognizes a threshold output of the first output α1 according to a threshold, and acquires an anaerobic threshold corresponding to the user according to the threshold output. In the present exemplary embodiment, the converting module 13 takes a first heart rate corresponding to the threshold output in the R-R interval as the anaerobic threshold corresponding to the user. It should be noticed that the anaerobic threshold can be varied along with different physical fitness conditions of the user, which is described in detail below with reference of FIG. 3.

FIG. 3 is a table listing first outputs calculated by the exercise guiding system of the disclosure and the corresponding heart rates. In FIG. 3, the exercise guiding system 1 adopts a method of progressively increasing a load while the user rides a stationary exercise bike to exercise, where a load wattage is increased by 20-30 every 3 minutes, and according to the first output α1 calculated by the calculating module 12, the heart rate corresponding to a time point when the user enters the anaerobic respiration is taken as the anaerobic threshold. The threshold of the disclosure can be set to 1, and when the first output α1 is changed from being greater than 1 to less than 1, it is determined that the user enters the anaerobic exercise from the aerobic exercise, and the first output α1 being less than 1 for the first time (i.e. 0.933) is defined as the threshold output, and the anaerobic threshold corresponding to the user is the first heart rate of 136. However, the disclosure is not limited thereto. In order to confirm that the user enters the anaerobic exercise, in the disclosure, the first output α1 being less than 1 for more than one minute (i.e. 0.856) can be defined as the threshold output, and now the anaerobic threshold corresponding to the user is the first heart rate of 145. By using the first output α1 being less than 1 for more than one minute as the threshold output, a situation that the first output α1 is only temporarily less than 1, and the subsequent first outputs α1 are all greater than 1 is avoided, so as to improve accuracy of the disclosure. However, in the disclosure, the first output α1 entering a range of 1±δ for the first time can be defined as the threshold output, where δ can be adjusted according to an actual requirement, for example, δ=0.1.

Referring to FIG. 1 again, the output module 14 is coupled to the converting module 13. The output module 14 receives the anaerobic threshold from the converting module 13, and outputs an exercise guidance of the user according to the received anaerobic threshold. The exercise guidance can provide related recommendations of exercise, which includes exercise time, exercise mileage, user's optimal exercise heart rate, user's main energy supply system (including fat, carbohydrate), etc.

It should be noticed that the sensing module 11 of the present exemplary embodiment can be a sensor or a sensing circuit, which records the R-R interval of the user and stores the same to a memory of the exercise guiding system 1. The calculating module 12 and the converting module 13 can be program codes implemented by a software form or a firmware form, and the program codes can be executed by a processor of the exercise guiding system 1 to retrieve the R-R interval from the memory and operate the same to generate the anaerobic threshold. However, the disclosure is not limited thereto. The calculating module 12 and the converting module 13 can also be implemented by a calculating circuit and a converting circuit, where the calculating circuit receives the input R-R interval and the converting circuit outputs the anaerobic threshold. After the anaerobic threshold is calculated, the processor can retrieve the exercise guidance of the user from the memory according to the anaerobic threshold and output the same through the output module 14. The output module 14 can be an output device such as a display, a speaker, etc. capable of guiding the user to learn the exercise guidance through visual perception or sense of hearing.

Figure 4:
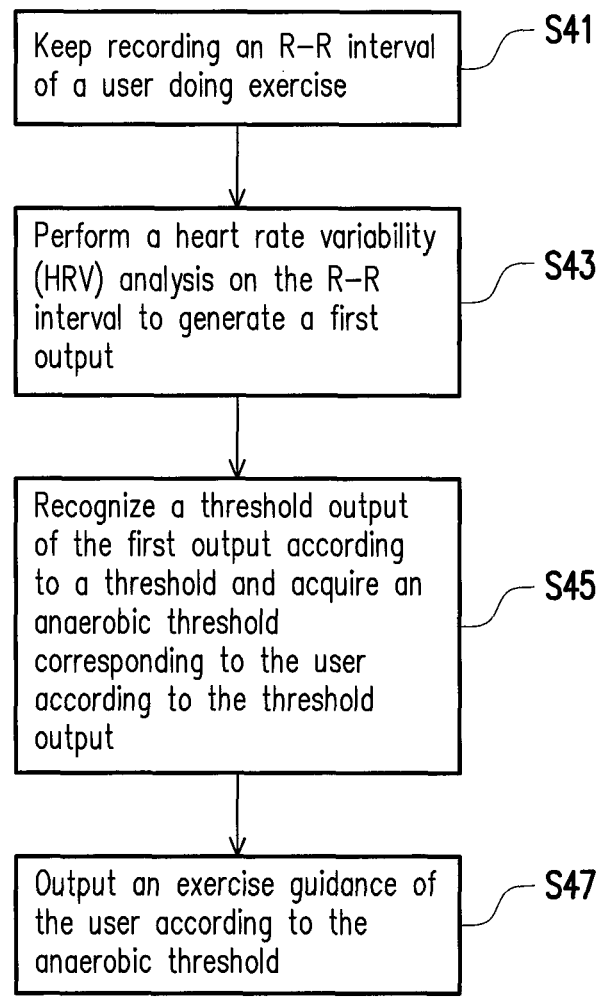
FIG. 4 is a flowchart illustrating an exercise guiding method according to the first exemplary embodiment of the disclosure.

FIG. 4 is a flowchart illustrating an exercise guiding method according to the first exemplary embodiment of the disclosure.

Referring to FIG. 4, in step S41, the sensing module 11 keeps recording an R-R interval of a user doing exercise.

In step S43, the calculating module 12 performs a HRV analysis on the R-R interval to generate a first output.

In step S45, the converting module 13 recognizes a threshold output of the first output according to a threshold and acquires an anaerobic threshold corresponding to the user according to the threshold output.

In step S47, the output module 14 outputs an exercise guidance of the user according to the anaerobic threshold.

Second Exemplary Embodiment

The exercise guiding system of the second exemplary embodiment is substantially the same to the exercise guiding system of the first exemplary embodiment, and a difference there between is that in the second exemplary embodiment, the calculating module performs the HRV analysis on the R-R intervals according to a time sequence, and the R-R intervals are sorted according to the time sequence, and a frequency domain parameter of the HRV analysis is calculated according to the sorted time sequence, and the first output is calculated according to the frequency domain parameter.

A structure of the exercise guiding system of the second exemplary embodiment is the same to the structure of the exercise guiding system of the first exemplary embodiment, and a difference between the first exemplary embodiment and the second exemplary embodiment is described below with reference of FIG. 1.

Referring to FIG. 1, the exercise guiding system 1 of the second exemplary embodiment includes the sensing module 11, the calculating module 12, the converting module 13 and the output module 14.

The sensing module 11 keeps recording a plurality sets of heartbeat information of the user doing exercise. Collection of the heartbeat information can be implemented through any in vitro sensor capable of detecting heartbeats of human body. The in vitro sensor can be coupled to the sensing module 11, such that the sensing module 11 can record the heartbeat information of the user. For example, the heartbeat information of the disclosure is R-R interval. It should be noticed that although the sensing module 11 of the disclosure directly obtains the sensed R-R intervals of heartbeats of the user from the in vitro sensor, the disclosure is not limited thereto. For example, in another exemplary embodiment, the sensing module 11 can also calculate the R-R intervals of the heartbeats of the user according to user's heart rate detected by the in vitro sensor.

The calculating module 12 is coupled to the sensing module 11. The calculating module 12 receives the R-R intervals corresponding to the user from the sensing module 11 and performs a HRV analysis on the R-R intervals to generate the first output $\alpha 1$.

Figure 5:
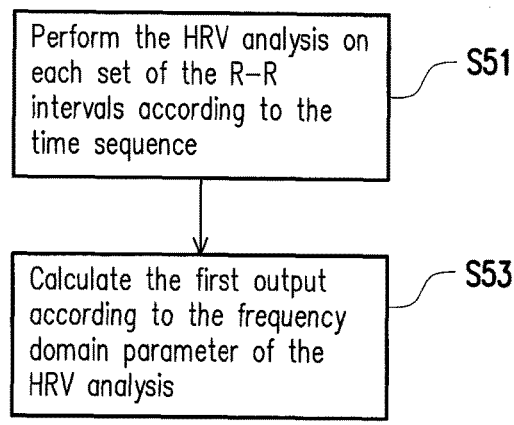
FIG. 5 is a flowchart illustrating a method for calculating the first output according to a second exemplary embodiment of the disclosure.

FIG. 5 is a flowchart illustrating a method for calculating the first output according to the second exemplary embodiment of the disclosure.

Referring to FIG. 5, in step S51, the calculating module 12 performs the HRV analysis on each set of the R-R intervals according to the time sequence. For example, in the step S51, the calculating module 12 sorts the R-R intervals of the user according to the time sequence.

Then, in step S53, the calculating module 12 calculates a frequency domain parameter of the HRV analysis according to the sorted time sequence, and calculates the first output $\alpha 1$ according to the frequency domain parameter. For example, the calculating module 12 converts the time sequence into a high frequency parameter HF and a low frequency parameter LF, and obtains the first output $\alpha 1$ according to a following equation (1).

$$\alpha 1 \sim 2/(1+HF/LF) \qquad (1)$$

It should be noticed that, the high frequency parameter is selected from a band range of 0.15 Hz to 0.40 Hz, and the high frequency parameter is a variance of the R-R intervals of the band range from 0.15 Hz to 0.40 Hz, which is mainly influenced by respiration, and represents an activity index of a parasympathetic nerve. The low frequency parameter is selected from a band range of 0.04 Hz to 0.15 Hz, and the low frequency parameter is a variance of the R-R intervals of the band range from 0.04 Hz to 0.15 Hz, which represents an activity index of a sympathetic nerve or an index for simultaneous control of the parasympathetic nerve and the sympathetic nerve.

Referring to FIG. 1, the converting module 13 is coupled to the calculating module 12, and the converting module 13 receives the first output $\alpha 1$ from the calculating module 12, recognizes a threshold output of the first output $\alpha 1$ according to a threshold, and acquires an anaerobic threshold corresponding to the user according to the threshold output. In the present exemplary embodiment, the converting module 13 takes a first heart rate corresponding to the threshold output in the R-R interval as the anaerobic threshold corresponding to the user. The output module 14 is coupled to the converting module 13. The output module 14 receives the anaerobic threshold from the converting module 13, and outputs an exercise guidance of the user according to the received anaerobic threshold.

It should be noticed that the sensing module 11 can be a sensor or a sensing circuit, and the calculating module 12 and the converting module 13 can be program codes implemented by a software form or a firmware form, or can also be implemented by a calculating circuit and a converting circuit. The output module 14 can be an output device such as a display, a speaker, etc. capable of guiding the user to learn the exercise guidance through visual perception or sense of hearing.

Third Exemplary Embodiment

The exercise guiding system of the third exemplary embodiment is substantially the same to the exercise guiding system of the second exemplary embodiment, and a difference there between is that in the third exemplary embodiment, the exercise guiding system further includes a database module, which stores status information of the user, and includes a correction module, which provides correction information complied with a physical status of the user according to the status information, and calculates the first output with better accuracy.

Figure 6:
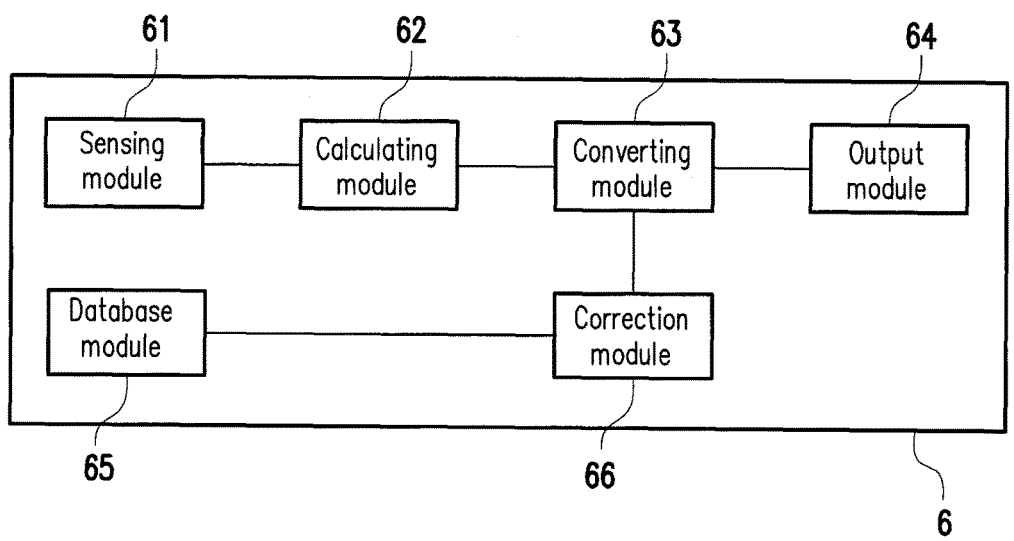
FIG. 6 is a block diagram of an exercise guiding system according to a third exemplary embodiment of the disclosure.

FIG. 6 is a block diagram of an exercise guiding system according to the third exemplary embodiment of the disclosure.

Referring to FIG. 6, the exercise guiding system 6 of the disclosure can calculate an anaerobic threshold corresponding to a time point when the user doing exercise enters an anaerobic respiration according to an exercise status of the user doing the exercise, and provide an exercise guidance according to the anaerobic threshold. The exercise guiding system 6 includes a sensing module 61, a calculating module 62, a converting module 63, an output module 64, a database module 65 and a correction module 66. It should be noticed that the exercise guiding system 6 can be installed on an electronic product, a portable electronic product, a watch, a wearable device, exercise equipment, a bicycle, a treadmill, glasses and a biosensor, etc., and exercises suitable for the exercise guiding system 6 includes at least one of a bicycle exercise, an aerobic exercise and running.

The sensing module 61 can keep recording a plurality sets of heartbeat information of the user doing exercise. Collection of the heartbeat information can be implemented through any in vitro sensor capable of detecting heartbeats of human body. The in vitro sensor can be coupled to the sensing module 61, such that the sensing module 61 can record the heartbeat information of the user. For example, the heartbeat information of the disclosure is R-R interval. It should be noticed that although the sensing module 61 of the disclosure directly obtains the sensed R-R intervals of heartbeats of the user from the in vitro sensor, the disclosure is not limited thereto. For example, in another exemplary embodiment, the sensing module 61 can also calculate the R-R intervals of the heartbeats of the user according to user's heart rate detected by the in vitro sensor.

The calculating module 62 is coupled to the sensing module 61. The calculating module 62 receives the R-R intervals corresponding to the user from the sensing module 61 and performs a HRV analysis on the R-R intervals to generate the first output $\alpha 1$.

The converting module 63 is coupled to the calculating module 62. The converting module 63 receives the first output $\alpha 1$ from the calculating module 62, recognizes a threshold output of the first output $\alpha 1$ according to a threshold, and acquires an anaerobic threshold corresponding to the user according to the threshold output, wherein the anaerobic threshold corresponding to the user is a first heart rate corresponding to the threshold output in the R-R interval.

The correction module 66 is coupled to the converting module 63. The correction module 66 receives the status information and provides correction information to the converting module 63 according to the status information. The converting module 63 obtains the anaerobic threshold corresponding to the user according to the threshold output and the correction information. The status information can be one of an exercise mode and health information, and the correction information may include various heart rates of the user, an exercise strength, an exercise time, a HRV parameter, a variation speed of the HRV parameter, and time domain information of HRV, which is used for setting the time point when the user enters the anaerobic respiration.

The database module 65 is coupled to the correction module 66 and stores the status information.

The output module 64 is coupled to the converting module 63. The output module 64 receives the anaerobic threshold from the converting module 63, and executes energy supply mode analysis according to the received anaerobic threshold to output the exercise guidance of the user. The exercise guidance can provide related recommendations of exercise, which includes exercise time, exercise mileage, user's optimal exercise heart rate, user's main energy supply system (including fat, carbohydrate), etc.

It should be noticed that the same to the first exemplary embodiment, implementations of the sensing module 61, the calculating module 62, the converting module 63 and the output module 64 of the present exemplary embodiment can be the same with that of the sensing module 11, the calculating module 12, the converting module 13 and the output module 14 of the first exemplary embodiment. Namely, the sensing module 61 can be a sensor or a sensing circuit, and the calculating module 62 and the converting module 63 can be program codes implemented by a software form or a firmware form, or can also be implemented by a calculating circuit and a converting circuit. The output module 54 can be an output device such as a display, a speaker, etc. capable of guiding the user to learn the exercise guidance through visual perception or sense of hearing. Moreover, in the present exemplary embodiment, the database module 65 can be stored in the memory of the exercise guiding system 6 and stores the status information, and the correction module 66 can be program codes implemented by a software form or a firmware form, and the program codes can be executed by a processor of the exercise guiding system 6 to retrieve the status information from the memory and convert the same into the correction information for transmitting to the converting module 63, so as to correct the first output $\alpha 1$. However, the disclosure is not limited thereto. The correction module 66 can also be implemented by a correction circuit, which receives the input status information and outputs the correction information to the converting module 63.

FIG. 7 is a comparison table of anaerobic thresholds obtained by using a gas analyser through a $VO_2$ max test and obtained through calculation of the exercise guiding system of the disclosure. In the $VO_2$ max test, a method of progressively increasing an exercise load is adopted, and three 27 years old testers ride stationary exercise bikes to exercise, where a load wattage is increased by 20-30 every 3 minutes, and analysis is simultaneously performed by using the gas analyser and the exercise guiding system of the disclosure. The gas analyser performs a respiratory exchange rate (RER) analysis, and when a value of the RER is equal to 1, it is determined that the user enters an anaerobic respiration state. In the exercise guiding system of the disclosure, when the first output $\alpha 1$ keeps being smaller than 1 for more than one minute, it is determined that the user enters the anaerobic respiration state, and the heart rate (HR) corresponding to the time point when the user enters the anaerobic respiration state is taken as the anaerobic threshold.

In FIG. 7, the above test is performed on three samples. A time for the sample 1 entering the anaerobic threshold of the exercise guiding system of the disclosure is 17 minutes, and the corresponding heart rate thereof is 145 bpm (beats per minute), and the time required for entering the anaerobic threshold based on the RER analysis is 19 minutes, and the corresponding heart rate thereof is 153 bpm. A time for the sample 2 entering the anaerobic threshold of the exercise guiding system of the disclosure is 23 minutes, and the corresponding heart rate thereof is 167 bpm, and the time required for entering the anaerobic threshold based on the RER analysis is 21 minutes, and the corresponding heart rate thereof is 163 bpm. A time for the sample 3 entering the anaerobic threshold of the exercise guiding system of the disclosure is 23 minutes, and the corresponding heart rate thereof is 122 bpm, and the time required for entering the anaerobic threshold based on the RER analysis is 21 minutes, and the corresponding heart rate thereof is 119 bpm.

FIG. 8 is a comparison table of anaerobic thresholds obtained by using a general equation, the exercise guiding system of the disclosure and the gas analyser through the $VO_2$ max test. In FIG. 8, since ages of the sample 1 to the sample 3 are all 27 years old, the anaerobic thresholds deduced according to the general equation are all 154 bpm, though the anaerobic thresholds of the sample 2 and the sample 3 obtained through the $VO_2$ max test are obviously different, and this is because that the users with the same age have different anaerobic thresholds according to different physical fitness conditions thereof.

FIG. 9 is a comparison table of percentages between heart rates corresponding to the anaerobic exercise and the maximum heart rate that are inversely deduced according to anaerobic thresholds obtained by using a general equation, the exercise guiding system of the disclosure and the gas analyser through the $VO_2$ max test. In FIG. 9, according to the results of the sample 1 to the sample 3, the exercise guiding system of the disclosure and the $VO_2$ max test respectively have errors of 4%, 1%, 1% in view of percentages between the heart rates corresponding to the anaerobic exercise and the maximum heart rate.

Referring to FIG. 7, FIG. 8 and FIG. 9, compared to the general equation, the anaerobic thresholds obtained according to the exercise guiding system of the disclosure are relatively accurate. Compared to the $VO_2$ max test, the exercise guiding system of the disclosure can achieve an effect of accurately detecting the anaerobic thresholds without using expansive equipment or wearing a breath analyser during the exercise.

Figure 10:
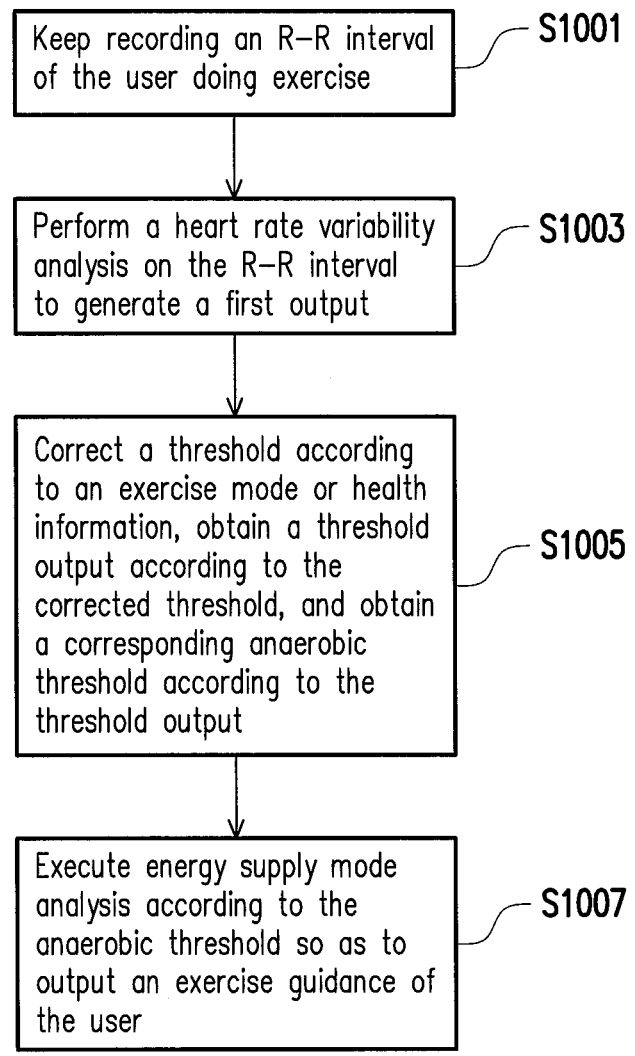
FIG. 10 is a flowchart illustrating an exercise guiding method according to the third exemplary embodiment of the disclosure.

FIG. 10 is a flowchart illustrating an exercise guiding method according to the third exemplary embodiment of the disclosure.

Referring to FIG. 10, in step S1001, the sensing module 61 keeps recording an R-R interval of the user doing exercise.

In step S1003, the calculating module performs a heart rate variability analysis on the R-R interval to generate a first output.

In step S1005, the converting module 63 corrects a threshold according to an exercise mode or health information of the correction module 66, obtains a threshold output according to the corrected threshold, and obtains a corresponding anaerobic threshold according to the threshold output.

In step S1007, the output module 64 executes energy supply mode analysis according to the anaerobic threshold so as to output an exercise guidance of the user.

FIG. 11 is a comparison table of energy supply mode analysis between the exercise guiding system of the disclosure and the $VO_2$ max test performed through the gas analyser. In FIG. 11, when the RER of the gas analyser is smaller than 0.85, it represents that the user is doing a low strength exercise and consumes fat; when the RER is between 0.85 and 1, it represents that the user is having a rest and consumes protein; when the RER is greater than 1, it represents that the user is doing a high strength exercise and consumes glucose. When the first output $\alpha 1$ of the disclosure is smaller than the threshold output and the user is in an exercise state, it represents that the user is doing the low strength exercise and consumes fat; when the first output $\alpha 1$ is smaller than the threshold output and the user is in a non-exercise state, it represents that the user is having a rest and consumes protein; when the first output $\alpha 1$ is greater than the threshold output, it represents that the user is doing the high strength exercise and consumes glucose. According to FIG. 11, the energy supply mode analysis can be correctly executed, so as to output the exercise guidance of the user.

In summary, in the exercise guiding system of the disclosure, the heart rate variability analysis is used in collaboration with the exercise mode and health information to deduce the anaerobic threshold of the user doing exercise, i.e. the heart rate corresponding to a time point when the user enters the anaerobic exercise from the aerobic exercise. By comparing the anaerobic threshold calculated by the exercise guiding system with the anaerobic threshold obtained through the $VO_2$ max test by using the gas analyser, the inversely deduced percentages between the heart rates corresponding to the anaerobic exercise and the maximum heart rate only have errors below 10%, and the exercise guiding system of the disclosure is unnecessary to use the expansive gas analyser. Therefore, the exercise guiding system of the disclosure can provide a personal computing on the anaerobic threshold without a limitation of user' age, and deduce the anaerobic threshold according to the heart rate variability analysis, such that the anaerobic threshold with a high accuracy can be calculated in a low cost.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. An exercise guiding system, comprising:
   a sensing module, keeping recording a plurality sets of R-R intervals of a user doing exercise;
   a calculating module, coupled to the sensing module, wherein the calculating module receives the plurality sets of R-R intervals corresponding to the user from the sensing module and performs a heart rate variability analysis on the plurality sets of R-R intervals to generate a plurality of first outputs;
   a converting module, coupled to the calculating module, wherein the converting module receives the first outputs from the calculating module, recognizes a threshold output in the first outputs according to a threshold and acquires an anaerobic threshold corresponding to the user according to the threshold output, wherein the anaerobic threshold corresponding to the user is a first heart rate corresponding to the threshold output in the plurality sets of R-R intervals, wherein the anaerobic threshold is a turning point of metabolism when the user's body is changed from an aerobic energy system to an anaerobic energy system during doing the exercise; and an output module, coupled to the converting module, wherein the output module receives the anaerobic threshold from the converting module and outputs an exercise guidance of the user according to the anaerobic threshold wherein the calculating module calculates a cumulative deviation between each heartbeat and an average heartbeat of the user for each set of the R-R intervals to generate a time sequence, wherein the calculating module cuts the time sequence into a plurality of sections with a predetermined length, and calculates a partial trending value of each of the sections according to a least square method, wherein the calculating module subtracts the time sequence by the partial trending value of each of the sections, and calculates a root mean square of each of the sections to generate a wave function, wherein the calculating module draws a plan diagram of a logarithm of the wave function relative to a logarithm of the predetermined length, wherein the calculating module calculates a linear equation of points in the plan diagram according to the least square method, and calculates a slope of the linear equation to obtain each of the first outputs.

2. The exercise guiding system as claimed in claim 1, further comprising:
a correction module, coupled to the converting module, wherein the correction module receives status information, and provides correction information to the converting module according to the status information,
wherein the converting module obtains the anaerobic threshold corresponding to the user according to the threshold output and the correction information.

3. The exercise guiding system as claimed in claim 2, further comprising:
a database module, coupled to the correction module, wherein the database module stores the status information, and the status information is one of an exercise mode and health information.

4. The exercise guiding system as claimed in claim 1, wherein the calculating module performs the heart rate variability analysis on each set of the R-R intervals according to a time sequence, converts the time sequence into a frequency domain parameter, and calculates each of the first outputs according to the frequency domain parameter.

5. The exercise guiding system as claimed in claim 4, wherein the frequency domain parameter comprises at least one high frequency parameter and a low frequency parameter.

6. The exercise guiding system as claimed in claim 5, wherein the high frequency parameter is selected from a band range of 0.15 Hz to 0.40 Hz, and the high frequency parameter is a variance of the plurality sets of R-R intervals of the band range.

7. The exercise guiding system as claimed in claim 5, wherein the low frequency parameter is selected from a band range of 0.04 Hz to 0.15 Hz, and the low frequency parameter is a variance of the plurality sets of R-R intervals of the band range.

8. An exercise guiding method, comprising:
keeping recording a plurality sets of R-R interval of a user doing exercise;

performing a heart rate variability analysis on the plurality sets of R-R intervals to generate a plurality of first outputs;

recognizing a threshold output in the first outputs according to a threshold, and acquiring an anaerobic threshold corresponding to the user according to the threshold output, wherein the anaerobic threshold corresponding to the user is a first heart rate corresponding to the threshold output in the plurality sets of R-R intervals, wherein the anaerobic threshold is a turning point of metabolism when the user's body is changed from an aerobic energy system to an anaerobic energy system during doing the exercise; and outputting an exercise guidance of the user according to the anaerobic threshold, wherein the step of performing the heart rate variability analysis on the plurality sets of R-R intervals to generate the first outputs comprises:

calculating a cumulative deviation between each heartbeat and an average heartbeat of the user for each set of the R-R intervals to generate a time sequence corresponding to each set of the R-R interval's;

cutting the time sequence into a plurality of sections with a predetermined length, and calculating a partial trending value of each of the sections according to a least square method;

subtracting the time sequence by the partial trending value of each of the sections, and calculating a root mean square of each of the sections to generate a wave function;

drawing a plan diagram of a logarithm of the wave function relative to a logarithm of the predetermined length; and calculating a linear equation of points in the plan diagram according to the least square method, and calculating a slope of the linear equation to obtain each of the first outputs.

9. The exercise guiding method as claimed in claim 8, further comprising:
receiving status information, and providing correction information according to the status information; and
obtaining the anaerobic threshold corresponding to the user according to the threshold output and the correction information.

10. The exercise guiding method as claimed in claim 9, further comprising:
storing the status information, wherein the status information is one of an exercise mode and health information.

11. The exercise guiding method as claimed in claim 8, wherein the step of performing the heart rate variability analysis on the plurality sets of R-R intervals to generate the first outputs comprises:
performing the heart rate variability analysis on each set of the R-R intervals according to a time sequence, converting the time sequence into a frequency domain parameter, and calculating each of the first outputs according to the frequency domain parameter.

12. The exercise guiding method as claimed in claim 11, wherein the frequency domain parameter comprises at least one high frequency parameter and a low frequency parameter.

13. The exercise guiding method as claimed in claim 12, wherein the high frequency parameter is selected from a band range of 0.15 Hz to 0.40 Hz, and the high frequency parameter is a variance of the plurality sets of R-R intervals of the band range.

14. The exercise guiding method as claimed in claim 12, wherein the low frequency parameter is selected from a band range of 0.04 Hz to 0.15 Hz, and the low frequency parameter is a variance of the plurality sets of R-R intervals of the band range.

15. An anaerobic threshold measuring method, comprising:
   calculating a plurality of time sequences of a plurality sets of R-R intervals corresponding to a user;
   calculating the time sequences to generate a plurality of R-R interval self-similarity parameters;
   recognizing a threshold parameter in the R-R interval self-similarity parameters according to a threshold, and acquiring an anaerobic threshold corresponding to the user according to the threshold parameter, wherein the anaerobic threshold corresponding to the user is a first heart rate corresponding to the threshold parameter in the plurality sets of R-R intervals, wherein the anaerobic threshold is a turning point of metabolism when the user's body is changed from an aerobic energy system to an anaerobic energy system during doing the exercise; and
   outputting an exercise guidance of the user according to the anaerobic threshold,
   wherein the step of calculating the time sequences to generate the R-R interval trending values comprises:
      cutting the time sequences into a plurality of sections with a predetermined length, and calculating a partial trending value of each of the sections according to a least square method, so as to generate the R-R interval trending values.

16. The anaerobic threshold measuring method as claimed in claim 15, wherein the step of calculating the time sequences of the plurality sets of R-R intervals corresponding to the user comprises:
   calculating a cumulative deviation between each heartbeat and an average heartbeat for each set of the R-R intervals of the user, so as to generate the time sequences.

17. The anaerobic threshold measuring method as claimed in claim 16, wherein the step of calculating the time sequences to generate the R-R interval self-similarity parameters comprises:
   calculating the time sequences to generate a plurality of R-R interval trending values;
   calculating the R-R interval trending values to generate a plurality of R-R interval wave functions; and
   drawing a plurality of plan diagrams according to the R-R interval wave functions, and obtaining the R-R interval self-similarity parameters according to points in the plan diagrams.

18. The anaerobic threshold measuring method as claimed in claim 15, wherein the step of calculating the R-R interval trending values to generate the R-R interval wave functions comprises:
   subtracting the time sequence by the partial trending value of each of the sections, and calculating a root mean square of each of the sections to generate the R-R interval wave functions.

19. The anaerobic threshold measuring method as claimed in claim 17, wherein the step of drawing the plan diagrams according to the R-R interval wave functions, and obtaining the R-R interval self-similarity parameters according to the points in the plan diagrams comprises:
   drawing the plan diagrams of logarithms of the R-R interval wave functions relative to a logarithm of the predetermined length; and
   calculating a linear equation of the points in the plan diagrams according to the least square method, and calculating a slope of the linear equation to obtain the R-R interval self-similarity parameters.

20. The anaerobic threshold measuring method as claimed in claim 15, wherein the step of calculating the time sequences to generate the R-R interval self-similarity parameters comprises:
   converting the time sequences into a frequency domain parameter, and calculating the R-R interval self-similarity parameters according to the frequency domain parameter.

21. The anaerobic threshold measuring method as claimed in claim 20, wherein the frequency domain parameter comprises at least one high frequency parameter and a low frequency parameter.

22. The anaerobic threshold measuring method as claimed in claim 21, wherein the high frequency parameter is selected from a band range of 0.15 Hz to 0.40 Hz, and the high frequency parameter is a variance of the plurality sets of R-R intervals of the band range.

23. The anaerobic threshold measuring method as claimed in claim 21, wherein the low frequency parameter is selected from a band range of 0.04 Hz to 0.15 Hz, and the low frequency parameter is a variance of the plurality sets of R-R intervals of the band range.

* * * * *